United States Patent [19]

Milač et al.

[11] Patent Number: 5,527,906

[45] Date of Patent: Jun. 18, 1996

[54] PROCESS FOR THE PREPARATION OF CEFTRIAXON DISODIUM SALT HEMIHEPTAHYDRATE

[75] Inventors: Nataša H. Milač; Igor Langof; Boris Rusjakovski; Sandi Borišek, all of Ljubljana; Darja Jereb, Radomlje, all of Slovenia

[73] Assignee: LEK, tovarna farmacevtskih in kemicnik izdelkov, Slovenia

[21] Appl. No.: 9,957

[22] Filed: Jan. 27, 1993

[30] Foreign Application Priority Data

Jan. 28, 1992 [AT] Austria .................. 132/92

[51] Int. Cl.⁶ ............................. C07D 501/36
[52] U.S. Cl. ............................. 540/227; 540/226
[58] Field of Search ................. 540/226, 227

[56] References Cited

U.S. PATENT DOCUMENTS

| | | | |
|---|---|---|---|
| 4,327,210 | 4/1982 | Montavon et al. | 544/27 |
| 4,758,556 | 7/1988 | Dürckheimer et al. | 540/227 |
| 4,767,852 | 8/1988 | Ascher | 540/227 |
| 5,026,843 | 6/1991 | Riccardo et al. | 540/227 |
| 5,126,445 | 6/1992 | Martin | 540/227 |

OTHER PUBLICATIONS

An Encyclopedia of Chemicals, Drugs, and Biologicals, The Merck Index, Eleventh Edition, Merck & Co., Inc., Rahway, New Jersey, pp. 294–301, 165,166. (1989).

*Primary Examiner*—Nicholas Rizzo
*Attorney, Agent, or Firm*—Pollock, Vande Sande & Priddy

[57] ABSTRACT

A new and improved process for the preparation of ceftriaxon disodium salt hemiheptahydrate of formula I

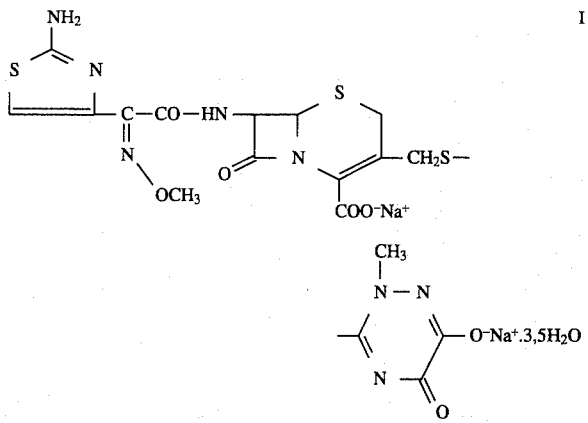

is described, wherein 7-amino-3-{[(2,5-dihydro-6-hydroxy-2-methyl-5-oxo-as-triazin-3-yl)thio]methyl}-3-cephem-4-carboxylic acid disodium salt is converted with a reactive 2-(2-aminothiazol-4-yl)-2-syn-metoxyimino acetic acid derivative such as 2-benzo-thiazolyl-thio ester in a water solution and in the presence of a suitable inert organic solvent such as acetone, at a temperature between 0° C. and 40° C. and then the desired compound is isolated in a very pure form and with a high total yield.

Ceftriaxon is a cephalosporin antibiotic of the third generation for parenteral application and a valuable agent for the treatment of heavy infections.

2 Claims, No Drawings

PROCESS FOR THE PREPARATION OF CEFTRIAXON DISODIUM SALT HEMIHEPTAHYDRATE

The present invention belongs to the field of pharmaceutical industry and relates to a new and improved process for the preparation of ceftriaxon disodium salt hemiheptahydrate of the formula I

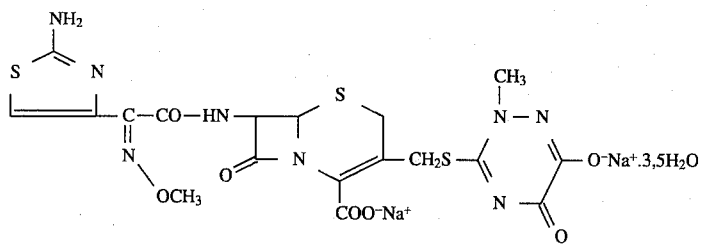

I

Ceftriaxon is a generic name for 7-{[2-(2-aminothiazol-4-yl)-2-syn-methoxyimino]-acetamido acetamido}-3-{[(2,5-dihydro-6-hydroxy-2-methyl-5-oxo-as-triazin-3-yl)thio]methyl }-3-cephem-4-carboxylic acid. The compound is a semisynthetic cephalosporin antibiotic of the third generation and is used in the form of disodium salt hemiheptahydrate for parenteral application in the treatment of heavy infections such as acute and chronic infections of the urinary tract, respiratory infections, endocarditis, meningitis etc.

In EP-B-0005830 there are described and claimed new derivatives of 7-[2-(2-amino-4-thiazolyl)-2-(methoxyimino)acetamido]-cephalosporanic acid of the general formula

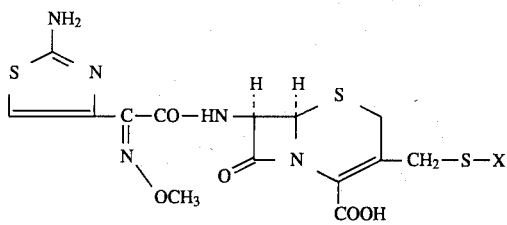

wherein X represents 2,5-dihydro-6-hydroxy-2-methyl-5-oxo-as-triazin-3-yl group or the corresponding tautomeric form thereof, i.e. 1,2,5,6-tetrahydro-2-methyl-5,6-dioxo-as-triazin-3-yl group according to the following structure

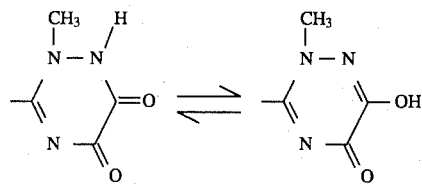

as well as esters/ethers and salts of this compound and hydrates thereof, the compounds of the above formula being present in the form of syn-isomer or anti-isomer or as a mixture of both isomeric forms.

As preferred products there are claimed (6R,7R)-7-[2-(2-amino-4-thiazolyl)-2-(7-methoxyimino)acetamido]-3-{[(2,5-dihydro-6-hydroxy-2-methyl-5-oxo-as-triazin-3yl)thio]methyl}-8-oxo-5-thia-1-azabicyclo[4.2.0]oct-2-en-2-carboxylic acid and salts thereof as well as the corresponding hydrates and hydrates of salts.

This compound is now known under the generic name of ceftriaxon. Ceftriaxon is a valuable cephalosporin antibiotic with a broad spectrum of activity against gram-positive as well as gram-negative microorganisms including Staphylococca producing β-lactamase, and various gram-negative bacteria producing β-lactamase such as *Pseudomonas aeruginosa, Haemophilus influenzae, Escherichia coli, Serratia marascens, Proteus* and *Klebsiella species*.

The process for the preparation is based on well-known methods for the preparation of structurally similar compounds as described in DE 25 27 291 and in the equivalent U.S. Pat. No. 4,091,211.

The synthesis of ceftriaxon according to the process described in EP-B-0005830 is based on cleaving the protecting group from the precursor thereof, i.e. from the compound of formula

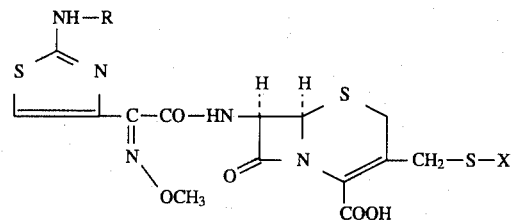

in which X has the above-mentioned meaning (keto-enol tautomerism), R represents an easily cleavable protecting group such as trityl or chloracetyl group, and the carboxy group can also be protected, and the subsequent conversion of ceftriaxon to salts or hydrates thereof and hydrates of the salts thereof.

Mono- or disalts of ceftriaxon can be prepared, wherein the formation of a disalt can be performed at the hydroxy group of the enol form, i.e. 2,5-dihydro-6-hydroxy-2-methyl-5-oxo-as-triazin-3-yl-group.

The possible preparation of alkaline and alkaline earth salts as well as of salts with organic bases such as mono- and diamines is described. The preparation of the hydrates is performed mostly automatically in the process of the preparation or as a result of the hygroscopic properties of the anhydrous product formed at the beginning.

For parenteral preparations a freeze-dried ceftriaxon disodium salt filled in ampulas can be prepared. Prior to application, the freeze-dried product is mixed with a 2% water solution of lidocainhydrochloride.

According to the process described in EP-B-0005830, the obtained syn/anti-mixture of the desired compound can be separated in a known manner, e.g. by recrystallization or by chromatographic methods using a suitable solvent or solvent mixture.

In the literature some further improved processes for the synthesis of ceftriaxon (as carboxylic acid) are described, which are based on the selection of new and improved acylating agents, i.e. derivatives of 2-(2-aminothiazol-4-yl)-2-syn-methoxyimino-acetic acid present in a syn-isomeric form with a great purity, whereat the syn-configuration is maintained in all steps of the conversion as well as in the acylating step.

By previously known derivatives capable of reaction, particularly by activated esters, it is possible that during the conversion, because of the rather unstable syn-configuration, it comes to an increased portion of anti-isomers and therefore to a lower yield of the desired syn-isomer.

By the use of improved acylating agents with a syn-configuration, the latter is maintained at the conversion and the desired substance (ceftriaxon) is obtained with both a great purity and yield; besides, there is no need to protect the amino substituent in the tiazolyl ring of the side chain as described in EP-A-0175814, DE 37 20 681 or in EP-A-0037380 and its equivalent U.S. Pat. No. 4,767,852. According to the latter process, 7-amino-3-(2,5-dihydro-2-methyl-6-hydroxy-5-oxo-as-triazin-3-yl)thiomethyl-3-cephem-4-carboxylic acid, in which the carboxy group is protected with trimethylsilyl group, is acylated by the new activated ester, i.e. by 2-(2-aminothiazol-4-yl)-2-syn-methoxyiminoacetic acid-2-benzthiazolyl-thioester.

By the protection of the carboxy group with the silylating agent, the solubility of the starting material, which in itself is very poorly soluble, is increased and, additionally, because of the hygroscopic properties of the silylating compound, the acylating takes place in an anhydrous medium and in an inert atmosphere.

After completing the acylation and isolation of ceftriaxon in a pure form and with a high yield (85%), ceftriaxon disodium salt could be prepared by a conversion of ceftriaxon (in the form of free acid) with sodium-2-ethylhexanoate in a relatively time-consuming manner, as described in EP-B-0005830.

In EP-A-0399094 an improved process for the preparation of ceftriaxon disodium salt hemiheptahydrate is described, in which 7-amino-3-{[(2,5-dihydro-2-methyl-6-hydroxy-5-oxo-as-triazin-3-yl)thio]methyl}-3-cephem-4-carboxylic acid in a water solution and an appropriate solvent in the presence of an amine selected from a group comprising trimethylamine, triethylamine, 1,4-dimethylpiperazine, N-ethylpiperidine, pyridine and dimethylaminopyridine is converted with 2-(2-aminothiazol-4-yl)-syn-methoxy-iminoacetic acid-2-benzothiazolyl-thioester. Subsequently, the obtained water solution of the formed salt is, without isolation, treated with a suitable salt of a base selected from a group consisting of dicyclohexylamine, diphenylamine, diisopropylamine, N-tert.-butylcyclohexylamine and N,N-dibenzylethylendiamine and the thus obtained precipitate is converted in a suitable solvent with sodium-2-ethylhexanoate to the desired compound. A yield of approx. 85% is indicated.

In this process the solubility of the poorly soluble starting compounds was increased by the preparation of the amine and triethylamine salt thereof, which at the same time resulted also in the protection of the carboxy group. Yet it is a disadvantage of this conversion that some secondary amines and salts thereof such as N,N-dibenzylethylendiamine-diacetate had to be specially prepared for the further use. By this time-consuming preparation of the conversion reagents, the very high total yield was decreased.

The invention is based on the task to prepare ceftriaxon disodium salt hemiheptahydrate in a new, improved and technologically easy manner, whereby the desired substance is obtained with a high total yield and a high purity, and the conversion steps take place in a water medium at a temperature around the ambient one and within short time.

This task is solved in such a manner that at first, simply by quantitative neutralisation of 7-amino-3-{[(2,5-dihydro-6-hydroxy-2-methyl-5-oxo-as-triazin-3-yl)-thio]-methyl}-3-cephem-4-carboxylic acid in the form of free acid with a water solution of sodium hydrogen carbonate, the disodium salt of this acid of the formula II

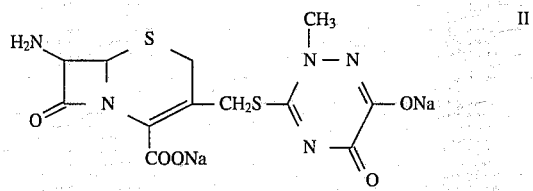

which is a new compound and has hitherto not been described in the literature. Subsequently, the obtained disodium salt is, without having been isolated from the water solution, acylated with the reactive 2-(2-aminothiazol-4-yl)-2-syn-methoxy-iminoacetic acid-2-benzothiazolyl-thioester in an suitable inert organic solvent such as acetone, at a temperature between 0° C. and 40° C., preferably at a temperature around the ambient one, and the title compound (ceftriaxon disodium salt hemiheptahydrate) is then isolated in a very pure form and with a high total yield.

The solubility of the starting compound 7-amino-{[(2,5-dihydro-6-hydroxy-2-methyl-5-oxo-as-triazin-3-yl)thio]methyl}-3-cephem-4-carboxylic acid is achieved in a simple manner by the quantitative neutralisation with sodium hydrogen carbonate in a water solution, whereby the time-consuming preparation of ceftriaxon disodium salt in the last step and the use of the expensive sodium-2-ethylhexanoate are avoided.

In addition, there is omitted the protection of the carboxy group in the starting compound as described in the above-mentioned patent literature, e.g. in EP-A-0037380.

As the acylating agent, there can be used a reactive 2-(2-aminothiazol-4-yl)-2-syn-methoxyimino acetic acid derivative, especially 2-benzothiazolyl-thioester thereof, which is known from the literature and described therein since it ensures the complete control of the geometry of —C=N-syn-configuration and thereby a high yield of the syn-isomer of the desired compound.

The course of the reaction, the identification and the content of the desired compound are determined by means of the high performance liquid chromatography (HPLC) in a weak basic ion exchanger (Lichosorb-$NH_2$) with a phosphate buffer/acetonitrile mixture as the mobile phase and UV detection a 270 nm. The purity of the desired compound is high and comparable with an authentic sample.

The invention is illustrated, yet in no way limited by the following examples.

EXAMPLE 7-amino-3-{[(2,5-dihydro-2-methyl-6-hydroxy-5-oxo-as-triazin- 3-yl )thio]methyl}-cephem-4-carboxylic acid (200 mg, 0.539 mmol) was suspended in water (4.5 ml), sodium hydrogen carbonate ($NaHCO_3$) (92 mg) was added and the suspension was stirred until it became clear. The obtained solution was then added under stirring to the separately prepared solution of 2-(2-aminothiazol-4-yl)-2-syn-methoxyiminoacetic acid-2-benzothiazolyl-thioester (230 mg, 0.656 mmol) in acetone (9 ml). After stirring for 4 hours at ambient temperature, the reaction mixture was filtered. Acetone (7 ml) was added to the filtrate up to cloudiness, then it was put to the freezer for 1 hour (whereat a precipitate was formed), then acetone (10 ml) was added thereto and the obtained reaction mixture was allowed to stand in the freezer overnight. Thereafter, a further portion of acetone (25 ml)

was added and it was cooled down in the freezer again, then the precipitated product was filtered off and dried under vacuum at ambient temperature. 7-{[2-(2-aminothiazol-4-yl)-2-syn-methoxyimino]acetamido}-3-{[(2,5-dihydro-6-hydroxy-2-methyl-5-oxo-as-triazin-3yl)thio]methyl}-3-cephem-4-carboxylic acid-disodium salt hemiheptahydrate (ceftriaxon disodium salt hemiheptahydrate) (325 mg, 91%) with a high purity was obtained. The analytical parameters were identical to those of the authentic sample.

$^1$H NMR-spectrum (DMSO) (δ, ppm) 6.76 5-thiazolyl (1H, s) 3.83 —OCH$_3$ (3H, s) 3.42 —NCH$_3$ (3H, s)

Reference Example 7-amino-3-{[(2,5-dihydro-6-hydroxy-2-methyl-5-oxo-as-triazin-3-yl)thio]methyl}-3-cephem-4-carboxylic acid (500 mg, 1.35 mmol) was suspended in water (10 ml) and sodium hydrogen carbonate (230 mg) was added thereto, then it was precipitated with 10 ml acetone and the resin-like product was allowed to stand in a freezer over night, then it was filtered off and suspended in acetone (30 ml). After stirring for 1 hour, the product was filtered off and dried in vacuum at 40° C. 7-amino-3-{[(2,5-dihydro-6-hydroxy-2-methyl-5-oxo-as-triazin-3-yl)thio]methyl}-3-cephem-4-carboxylic acid disodium salt in the form of a powder-like, light yellow product melting at a temperature above 200° C. was obtained.

We claim:

1. A process for the preparation of 7-{[2-(2-aminothiazol-4-yl)-2-syn-methoxyimino]acetamido}-3-{[(2,5-dihydro-6-hydroxy-2-methyl-5-oxo-as-triazin-3-yl)thio]methyl}-3-cephem-4-carboxylic acid disodium salt hemiheptahydrate (ceftriaxon disodium salt hemiheptahydrate) of the formula I

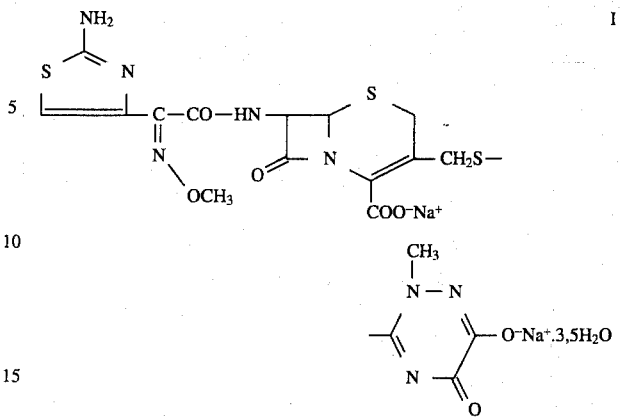

which comprises acylating 7-amino-3-{[(2,5-dihydro-6-hydroxy-2-methy-5-oxo-as-triazin-3-yl)-thio]methyl}cephem-4-carboxylic acid with 2-(2-aminothiazol-4-yl)-2-syn-methoxyimino acetic acid-2-benzothiazolyl thioester in the presence of sodium hydrogen carbonate in aqueous acetone at a temperature between 0° C. and 40° C., and thereby obtaining the ceftriaxon disodium salt hemiheptahydrate from the said reaction mixture in a substantially pure form suitable for therapy.

2. A process according to claim 1, wherein at least 2 moles of sodium hydrogen carbonate as to the starting compound are used.

* * * * *

UNITED STATES PATENT AND TRADEMARK OFFICE
CERTIFICATE OF CORRECTION

PATENT NO. : 5,527,906
DATED : June 18, 1996
INVENTOR(S) : Milac et al.

It is certified that error appears in the above-indentified patent and that said Letters Patent is hereby corrected as shown below:

```
Column 1, line 21, please change
"acetamido acetamido" to ---acetamido---
```

Signed and Sealed this

Twenty-second Day of July, 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,527,906
DATED : June 18, 1996
INVENTOR(S) : Milac, et. al.

It is certified that error appears in the above-indentified patent and that said Letters Patent is hereby corrected as shown below:

Title page, item [73], Assignee: should read--LEK, Tovarna farmacevtskih in kimičnih izdelkov, d.d., Slovenia--.

Signed and Sealed this

Twenty-first Day of October 1997

Attest:

BRUCE LEHMAN

*Attesting Officer*  *Commissioner of Patents and Trademarks*